United States Patent [19]

Ansorge et al.

[11] Patent Number: 5,347,122
[45] Date of Patent: Sep. 13, 1994

[54] LIGHT TRANSMISSION SYSTEM WITH PHOTON TRANSFER TO AN OPTICAL DETECTOR AND CELL INVESTIGATION TECHNIQUES USING THE LIGHT TRANSMISSION SYSTEM

[75] Inventors: Richard E. Ansorge; Clare E. Hooper, both of Cambridge; William W. Neale, Great Wilbraham; Philip Stanley, Cambridge, all of Great Britain

[73] Assignee: Cambridge Imaging Limited, Cambridge, Great Britain

[21] Appl. No.: 849,436

[22] PCT Filed: Dec. 10, 1990

[86] PCT No.: PCT/GB90/01920
§ 371 Date: May 15, 1992
§ 102(e) Date: May 15, 1992

[87] PCT Pub. No.: WO91/09300
PCT Pub. Date: Jun. 27, 1991

[30] Foreign Application Priority Data

Dec. 8, 1989 [GB] United Kingdom ............... 8927754

[51] Int. Cl.$^5$ ............................................. H01J 5/16
[52] U.S. Cl. ................................. 250/227.11; 385/120
[58] Field of Search ........... 250/227.2, 227.11, 227.23, 250/227.31, 205, 461.1, 461.2, 372, 367, 363.01; 385/120, 27, 29, 50; 356/244, 418, 419

[56] References Cited

U.S. PATENT DOCUMENTS 4,141,641  2/1979  Nagai et al. ......................... 385/120
4,978,195 12/1990  Takano et al. ...................... 385/120
5,074,683 12/1991  Tarn et al. .......................... 385/120

FOREIGN PATENT DOCUMENTS 8804045  6/1988  PCT Int'l Appl. .

Primary Examiner—David C. Nelms
Assistant Examiner—Que T. Le
Attorney, Agent, or Firm—Lee, Mann, Smith, McWilliams, Sweeney & Ohlson

[57] ABSTRACT

Apparatus as described by which very low light levels emitted typically by very small regions such as individual cells in cultured monolayers, can be more readily detected by a detector such as a CCD detector or image intensifier. The light capturing aid is a fibre optic face plate located between the light emitting material and the detector, but not in contact with the light emitting material. Where the latter is contained on a surface such as a petri dish, the face plate is positioned between the dish and the detector with at least an air gap between the face plate and the detector.

19 Claims, 5 Drawing Sheets

LIGHT TRANSMISSION SYSTEM WITH PHOTON TRANSFER TO AN OPTICAL DETECTOR AND CELL INVESTIGATION TECHNIQUES USING THE LIGHT TRANSMISSION SYSTEM

FIELD OF INVENTION

This invention concerns light transfer systems which image onto a light sensitive optical detectors and biomedical cell investigation techniques which rely on low level light detection and transmission which can be enhanced thereby. The invention has particular application to systems in which an image intensifier is optically coupled to a sample holder to enable photon emission emanating from differing sites on the sample holder to be detected. Such apparatus is especially useful for low light level detection particularly in the field of biomedicine, molecular biology and genetic engineering.

BACKGROUND TO THE INVENTION

Many biomedical tests and experiments rely on the visual assessment of cell and molecular activity of samples located on a holder such as microscope slide, Petri dish and the like. Some such activity produces photon emission as a natural consequence of the activity under review and in other studies molecular and cellular changes can be observed by the addition of material which will generate photonic emission such as is obtained using so-called lux, luc and phot gene technology.

Thus in the general fields of genetic engineering and molecular biology the study of gene expression, gene deletion and gene insertion has involved the addition of genetic material which will generate photon emission from genetically manipulated cells, using so-called lux gene expression, and such techniques have been used in the fields of virology, molecular biology, immunology, microbiology and cell biology.

Using apparatus as described PCT published specification WO88/04045, it should be possible to observe lux gene expression from molecular and cell activity at a very much earlier point in the reaction than has hitherto been the case, due to the great sensitivity of such apparatus. In particular it should be possible to identify the position of photon emission due to the lux gene expression from single cell locations, thereby allowing tests performed on very small samples of material and in very much smaller periods of time than hitherto. However if an ordinary Petri dish or microscope slide is employed as the sample holder, it is not possible to provide the perfect optical coupling needed between the photon emitting material of the sample and the input face of the fibre optic entrance window of the image intensifier, since the base of an ordinary Petri dish and the material of an ordinary microscope slide is not in the form of a fibre optic face plate.

It has been proposed to overcome this problem in the aforementioned PCT specification by forming the base of the Petri dish or the microscope slide from fibre optic glass and placing the underside of this material in intimate contact with the input window (also of fibre optic glass) of the image intensifier.

Whilst this should reduce the degradation of resolution in transferring light emanating from photon emitting sites onto the image intensifier, it has been found in practice that perfect contact is not always possible between the molecular or cellular material of the sample and the upper face of the sample holder, so that even when the latter is formed from fibre optic glass, serious resolution degradation results, due to spreading of light as it travels from the material in the sample to the fibre optic glass of the sample holder. This becomes particularly noticeable when the depth of the sample material becomes significant.

It is an object of the present invention to overcome this problem.

It is another object of the invention to provide improved methods of cell and molecular investigation which follow from the use of the improved light transfer system of the invention.

SUMMARY OF THE INVENTION

According to one aspect of the present invention in a light transmission system in which photon emission from material on a first surface is to be transferred to an optical detector a fibre optic face plate is located between the said first surface and the said detector and the position of the face plate therebetween is selected so as to form a focussed image of discrete photon emitting sites on the first surface, in the plane of the said detector.

The detector may be an image intensifier or intensified CCD camera or a cooled CCD detector.

The present invention can be applied to apparatus such as is described in the aforementioned PCT published specification WO88/04045 in which the sample holder is itself formed from fibre optic glass but surprisingly also allows conventional Petri dishes and microscope slides of plastics and ordinary glass to be employed. Thus it has been found that when the thickness of the sample is small in relation to the air gap between the sample holder and the fibre optic face plate and the gap between its outward face and viewing window of the image intensifier, then the fibre optic face plate should be positioned substantially midway between the sample holder and the viewing window of the image intensifier for optimum results.

If the sample holder thickness is significant then the face plate must be shifted so that it is midway in an optical sense, having due regard to the refractive index of the material from which the sample holder is made.

Although the overall contrast of the image produced by an arrangement embodying the invention is less than would be obtained if a conventional focussing lens were to be employed in the place of the fibre optic face plate, the light collecting properties of the face plate are considerably greater than those of a conventional lens insofar as small point sources of photon emission are concerned and where the material surrounding each point source of photon emission is non-photon emitting (i.e. dark), the contrast reduction is inconsequential.

The focussing effect of the intermediate fibre optic plate is optimised if the distances and materials involved satisfy the relationship:

$$a/n_1 = b/n_2$$

where a is the thickness of the sample holder and b is the thickness of the gap between the intermediate plate and the image intensifier; s and $n_1$ and $n_2$ are the refractive indices of the two materials.

A typical example is:

$$a = 0.8 \text{ mm}, n_1 = 1.4$$

$$b = 0.6 \text{ mm}, n_2 = 1.0$$

for a petri dish formed from plastics material with an air gap. The intermediate face plate of the invention would typically be a few centimeters in diameter and approximately 2 mm thick, and be formed from numerous 6 microns diameter optical fibres fused together, with the axes of the fibres all parallel, and all generally perpendicular to the end faces of the plate.

The invention is of particular application where it is important to be able to insert an optical filter between the sample holder and a detector such as an image intensifier. Thus according to a further aspect of the invention in a light transmission system as aforesaid the sample holder, face plate and detector are spaced and located so as to define at least one gap between the opposed parallel faces of either the holder and the face plate or the latter and the detector and an optical filter is inserted into the gap as required, and the relative positions of the holder, face plate and detector are selected so that the optical path between the holder and the face plate is substantially the same as that between the face plate and the detector having regard to the refractive index of the filter material.

If a particular test requires the insertion of a filter between one part of a test and another, then to avoid the need to alter the position of the face plate and/or viewing window, a neutral density filter of material having the same refractive index as the filter to be used in the test may be inserted in the gap when the filter is not required, but is removed and replaced by the filter when the latter is required to be in place.

The invention thus provides a light transmission system as aforesaid in which a gap for an optical filter to be inserted normally includes a neutral density filter of material having the same refractive index as the material of the optical filter, and means is provided whereby the neutral density filter can be substituted by the optical filter when required.

The invention also provides a method of detecting light emissions of a particular wavelength from small discrete regions on a support surface by means of a broad spectrum response detector coupled thereto by a face plate positioned between the support surface and the viewing window of the detector, comprising the step of inserting a neutral density filter during setting up (so that all light emanating from material on the support surface will be transferred to the detector to allow setting up to occur), then removing the neutral density filter and replacing same with a wavelength selective filter and detecting whether any light of the said wavelength is being emitted by the said material by inspecting the signal output of the detector.

This aspect of the invention is not limited to the positioning of wavelength selective filters in the gap but, as aforesaid, neutral density filters of differing attenuation may be inserted to increase the dynamic range of a given system at the top end (i.e. to enable a given system to handle light emitting materials which emit considerable quantities of light) without damaging or overloading the image intensifier.

Likewise the aspect of the invention is not limited to positioning one filter at a time, but envisages the use of a rotating or sliding carrier containing two or more different wavelength selecting filters (perhaps together with a neutral density filter), the carrier being positioned between the support containing the photon emitting material and the intermediate face plate of the invention (or between the face plate and the detector), and the carrier being movable manually or under power as by a solenoid or motor, to present different filters in the light path.

In addition the invention will permit a shutter to be positioned between the support surface bearing the light emitting material and the detector by locating a shutter mechanism such as iris diaphragm or a roller blind shutter in the gap between the sample support and the intermediate fibre optic face plate or between the latter and the detector.

A shutter as aforesaid may be combined with one or more wavelength selective filters if required.

In addition or instead an LCD matrix under electrical control as for example from a computer, may be positioned in a gap as aforesaid with or without a shutter and/or filter or filters to enable selective area masking to be performed. This may for example permit certain areas of the field of view to be masked to reduce the light emanating therefrom incident on the detector so that low light levels in a field may be examined without swamping by light from other "brighter" areas.

In addition the provision of a gap enables a detector such as an image intensifier to be employed having (as is conventional) a photocathode operating at typically 10,000 volts without the need for special precautions to isolate the photocathode from other items—particularly the sample holder. This advantage can be used to further effect in that the gap reduces any corona discharge effect.

Thus whilst the basic invention enables tissue sections, biopsy material, cell monolayers and cell suspensions (in media or solution) to be investigated when using gene DNA or antibody (monoclonal) medicated probes with luminescent or fluorescent labels, the further development using filters in the gap permitted by the invention, enables the determination of spectral characteristics relating to the above processes, for example dual wavelength fluorescence or both fluorescent and luminous measurements of the same tissue section or cellular monolayer to be made.

The invention thus encompasses methods of investigation as aforesaid in which the medium under investigation is carried on a sample support, light from which is transferred to a detector through a fibre optic face plate positioned therebetween as aforesaid with or without filters in the gap or gaps between the face plate and the sample support and the detector as required, and apparatus for performing any of these methods.

The release of Adnosine TriPhosphate (ATP) when cells are caused to lyse, can also be rendered visible by utilising a suitable reagent which causes photon emission when ATP is released.

The photon emission produced by the ATP release from the lysing of a single cell is very small, but can nevertheless be detected using apparatus as described in PCT/WO88/04045 in combination with the present invention. Thus according to another aspect of the invention a method of detecting the presence of particular cells in a sample comprises the steps of:

a) placing the sample on a sample holder together with luciferase and luciferin
b) positioning the latter in apparatus as aforesaid so that any photon emission from discrete regions of the sample will be transmitted via the face plate to the detector.
c) noting the output signal level of the detector
d) adding a lysing agent to the sample and noting any sudden increase in light emission from any particular region of the sample, as will be evidenced by a sudden increase in the detector output signal for such a region.

If no such local increase in light level is noted, then it can be assumed that the sample did not contain any cell of the type expected and vice versa.

It is to be noted that a very sensitive imaging method is essential for the success of this technique since the local amount of light emitted by the lysing of a single cell would not contribute sufficiently to be seen as a significant fluctuation of the overall light level (as would be seen by a photomultiplier tube (PMT) integrating the light emitted from the whole sample). Indeed the signal to noise ratio of a PMT would almost certainly prevent the lysing of a single cell from being detected. The present invention however does provide a sufficiently sensitive detection technique as to permit single cell lysing to be detected.

The invention thus also lies in a method as aforesaid for detecting the lysing of a single cell in a sample and in apparatus for performing that method.

As a corollary the toxicity of a material to cells of other material can be measured by adding the toxic material in known concentrations to a sample containing one or more cells of known material, together with luciferase and luciferin and in the manner as described aforesaid, observing whether there is any local photon emission activity due to individual cells lysing as they are attacked by the toxic material.

The invention is of particular advantage when investigating the infection of a monolayer of cells on a Petri dish with a genetically engineered virus which transmits lux (and other) genes into the genetic code of the cells. In such investigations, the culture is incubated for a period of time and as the cells become infected the luciferase enzyme is produced by single infected cells more commonly referred to as gene expression. After a period of time luciferin and ATP are added and light will be emitted from any sites of infection.

Historically the light emissions have been detected by using photographic film in contact with the Petri dish but such film is relatively insensitive and requires long exposure times and relatively high levels of photon emission. In practice this has meant incubation times have had to be sufficiently long to allow the infection of a single cell to spread to adjoining cells which together can produce enough light when the luciferin and ATP are added to expose the film. Sites of infected cells can then be seen by viewing the film through the dish and infected cells harvested using micropipette techniques and the like.

By using the present invention, infected cells can be found sooner (since it is only necessary to incubate for long enough for single cells to become infected). These can then be harvested at an earlier stage than previously.

Early harvesting has the further advantage that purer yield of a cloned virus is obtained. This is because the viral population on a culture dish will naturally tend to diffuse across the sample holder with time.

The invention can be used with any suitable detector. Thus an image intensifier may be used, but the techniques described may be used to advantage to allow light detectors to be used which otherwise would not be suitable for biomedical investigation. Thus, where an air gap can be provided between the sample and the detector as is possible using the invention, a cryogenically cooled CCD detector (operating for example at $-20°$ C.) may be employed. Historically the use of such detectors has had to be in combination with lenses which have limited the amount of light transferred to the detector. No such loss of light is experienced using the present invention and a cryogenic CCD camera may therefore be used as the detector.

Where the CCD camera includes a fibre optic plate entry window, this may comprise the fibre optic plate required by the invention where its spacing from the CCD surface and from the sample containing surface is appropriate.

Thus for example as employed herein, the term detector may comprise:
a) an image intensifier of the type described in PCT/WO88/04045, or
b) a CCD detector, (which may be cryogenically cooled).

The term "fibre optic face plate" as used herein is intended to refer to a plate of glass formed from a uniform circular cross section bundle of optical fibres the cross section diameter of which is typically 50 mm and the length of the fibres making up the bundle is typically 3 mm and the two faces of the plates are parallel and are spaced apart by the length of the fibures i.e. by 3 mm. Typically the fibres making up the plate are approximately 6 microns in diameter.

As already mentioned, the invention may be applied to the detection of light in many processes. Two examples are given by way of example.

In the first example, the object is to determine whether infected cells are present on a Petri dish, which is detectable due to expression of a luminescent luciferase gene.

Luciferase gene expression may be observed if a 50 mm diameter petri dish containing a cellular monolayer (approximately 1 million cells) is infected with a luciferase-virus recombinant (which expresses the luminescent luciferase gene). Infected cells will be seen as points of light in the field of view, representing cells expressing the luciferase gene. The cells, if viewed directly through the base of the petri dish appear as defocussed (and hence large) regions of light emission in the image. The use of a fibre optic plate and properly adjusted gap in accordance with the invention results in a much sharper image of the light emitting cells.

In a second example the lysing of individual microorganisms can be observed. In this case a 50 mm diameter petri dish containing 1 ml of sample reagent buffer (i.e. luciferase, luciferin and buffer) is viewed by direct contact imaging. Little of no light is observed. When this "background" level of light emission has been recorded as a reference a small volume (0.1 ml) of lysing agent is added and the bacteria selectively lysed. The selective (controlled) release of cell contents generates cell specific ATP which is measured by the presence of reagent buffer, resulting in light emission from the regions of the cells.

BRIEF DESCRIPTION OF THE DRAWINGS

The invention will now be described, by way of example with reference to the accompanying drawings, in which.

DESCRIPTION OF EXAMPLES EMBODYING THE BEST MODE OF THE INVENTION

Figure 1:
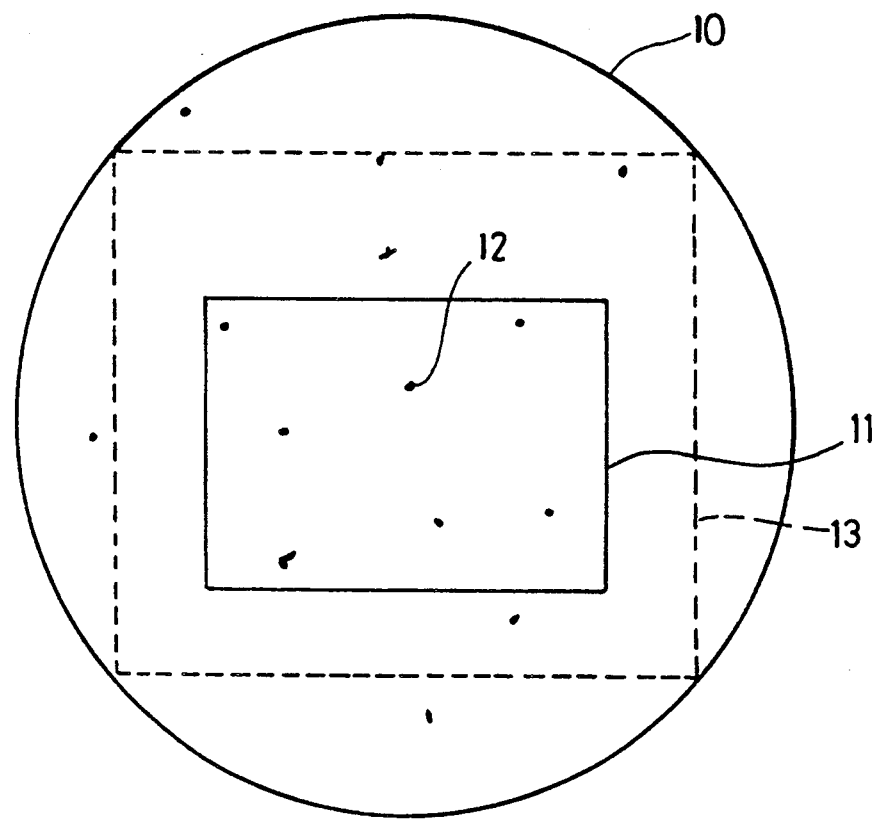
FIG. 1 is a plan view from above of a petri dish which is to be viewed from the underside for imaging purposes.

In FIG. 1 a petri dish 10 is shown containing a quantity of well spaced small light emitting cells (or regions) such as 12. The size of each such cell 12 is 30 microns and there might be fourteen or so such cells in a cellular monolayer containing ¼ million cells—the remaining ones of which are non-light emitting.

Figure 2:
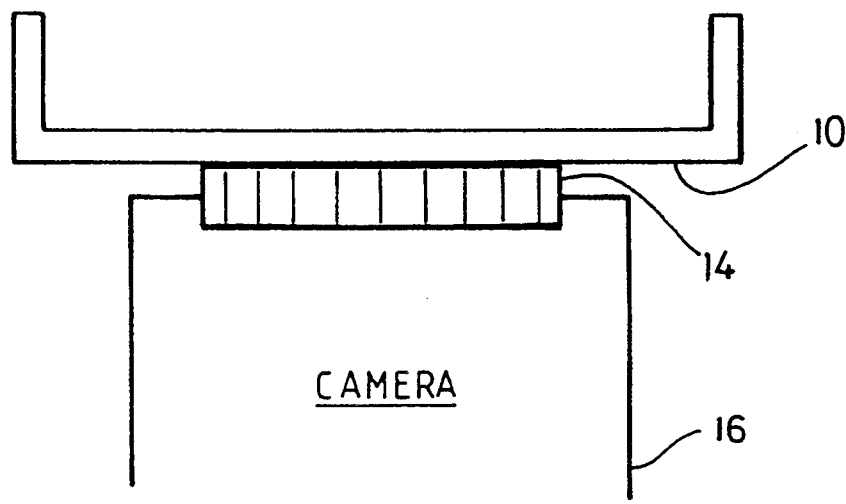
FIG. 2 illustrates a side view of a known arrangement for viewing a petri dish.
Figure 2A:
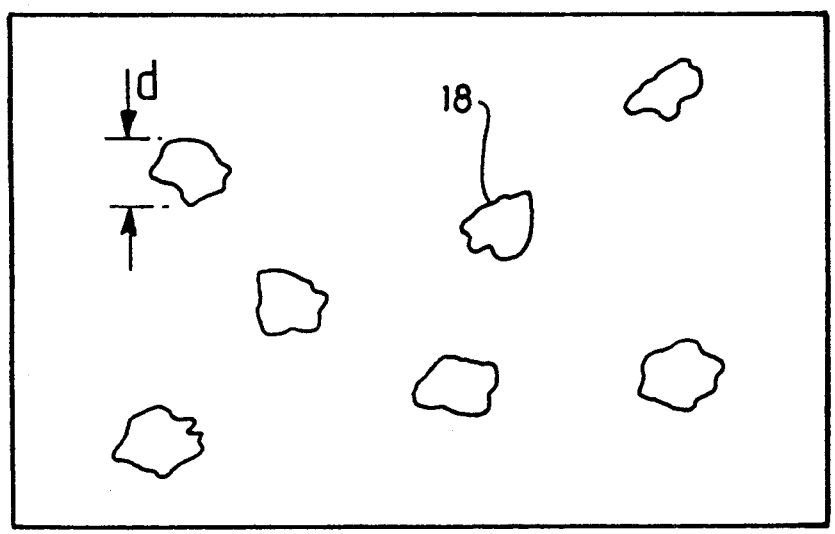
FIG. 2A is an example of an image as seen with the arrangement of FIG. 2.

Hitherto the viewing of the light emitting cells has been achived by fitting the underside of the petri dish 10 to a viewing window 14 of a camera 16 such as an interrupted CCD camera or an image intensifier (see FIG. 2A). The spread of light from each of the "point" sources such as 12 has produced relatively large areas of light on the viewing window of the camera such as 18 in FIG. 2A. These are many times the area of the light emitting cells and because of the spread of the light, are considerably less bright, and therefore less easy to distinguish from the background.

Figure 3:
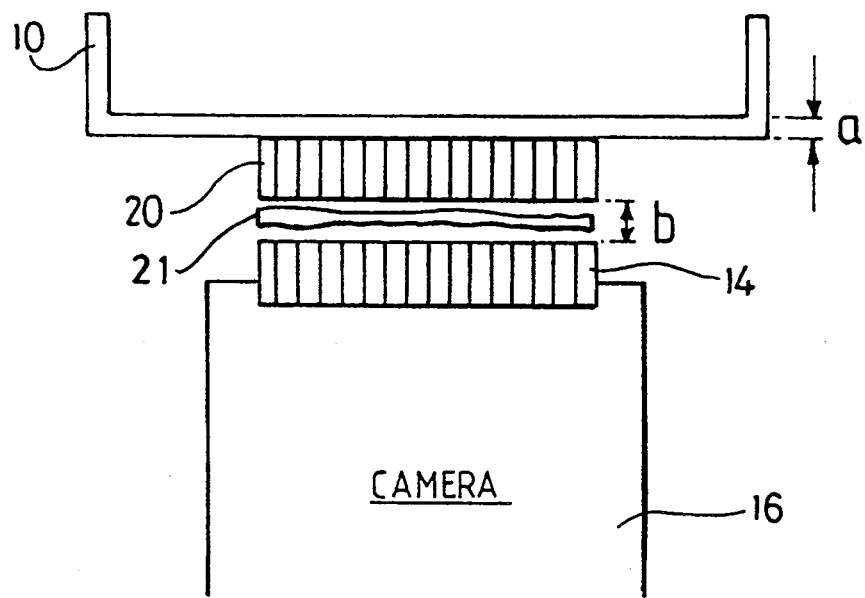
FIG. 3 illustrates a side view of an improved arrangement embodying the invention.
Figure 3A:
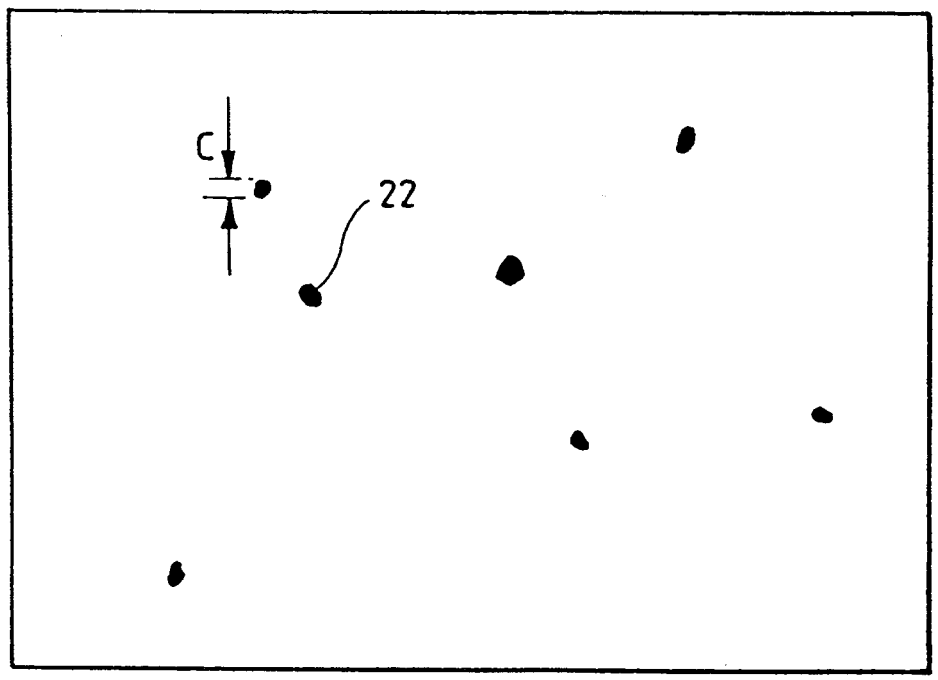
FIG. 3A is an example of an image as seen with the arrangement of FIG. 3.

If in accordance with the invention a fibre optic plate 20 is interposed between the underside of the petri dish 10 and the viewing window 14 of the camera 16 and a small air gap is left between the plate 20 and the window 14, a considerable improvement is obtained and the spots of light such as 22 corresponding to the cells appear smaller and brighter (as shown in FIG. 3) than the corresponding areas of light, such as 18, in FIG. 2.

A rotating or sliding carrier 21 containing a plurality of different filters may be positioned between the viewing window 14 and the plate 20 as shown in FIG. 3. The carrier 21 may be moveable to present different filters in the light path. Alternatively, the carrier 21 may instead be a shutter. The shutter can be combined with one or more filters.

It has been found that for best results the width of the air gap is related to the thickness of the base of the petri dish. If as shown in FIG. 3 the latter is denoted by a and the gap is denoted by b, then if the refractive index of the material forming the petri dish is $n_1$ and that of the gap (typically this will be air) is $n_2$, then $$a/n_1 = b/n_2$$

Since $n_2 = 1.0$ for air and the thickness of a petri dish base is usually 0.8 mm the gap can be expressed as a/n where n is the refractive index of the petri dish material (either plastics or glass).

Figure 4:
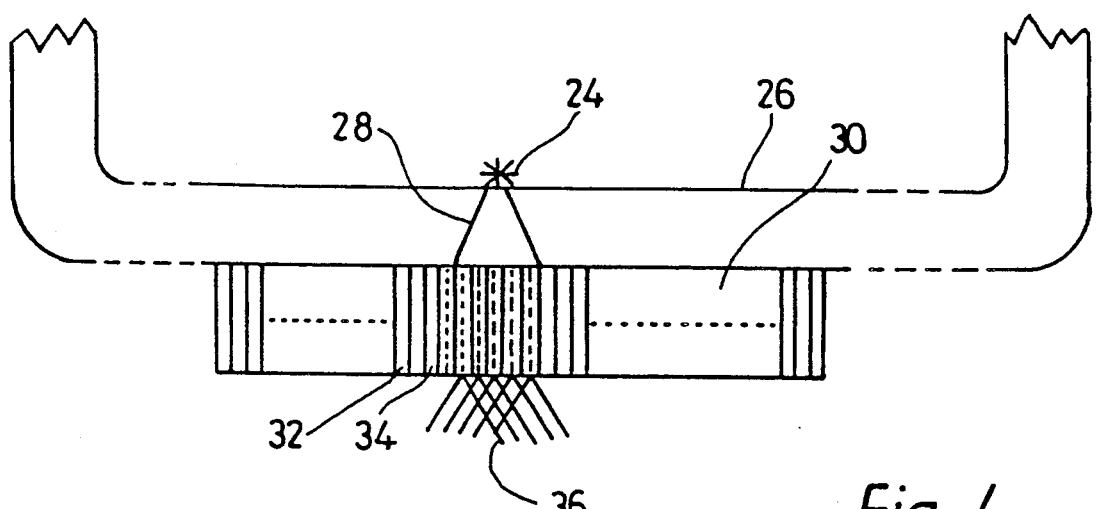
FIG. 4 is a side view showing diagrammatically how the invention is believed to work.

The manner by which the enhancement is achieved is perhaps best understood with reference to FIG. 4. Here a point source of light 24 is shown situated on the topside of a petri dish base 26. Light is emitted from the source 24 in all directions but the light of interest is that contained within the cone 28. This light enters the fibre optic plate 30 and the upper end of each optical fibre 32, 34 etc. can now be thought of as being a small point source of light the majority of the light from which passes downwardly through the optical fibre, to exit from the lower end. The exiting light from each fibre can be thought of as a small point source similar to 24, but displaced in space towards the viewing window of the camera (not shown). Each of the fibre ends will produce its own cone of light and because of the proximity of the fibres, some of the cones will overlap to produce a more intensely illuminated area 36 in the centre, as shown.

Whilst the more intensely illuminated area 36 will not be as bright as the point 24, and will be somewhat larger in area, it will be considerably brighter and much smaller than the area at the base of the cone 28.

The plane at which optimum intensification occurs will not necessarily be very well defined, but experiment has shown that if the petri dish has a thick base then the gap between the lower face of the plate 30 and the plane at which intensification is obtained, will need to be larger than is the case if the petri dish base thickness is thinner. It has also been observed that the gap is apparently inversely proportional to the refractive index of the material from which the petri dish base is constructed.

Figure 5:
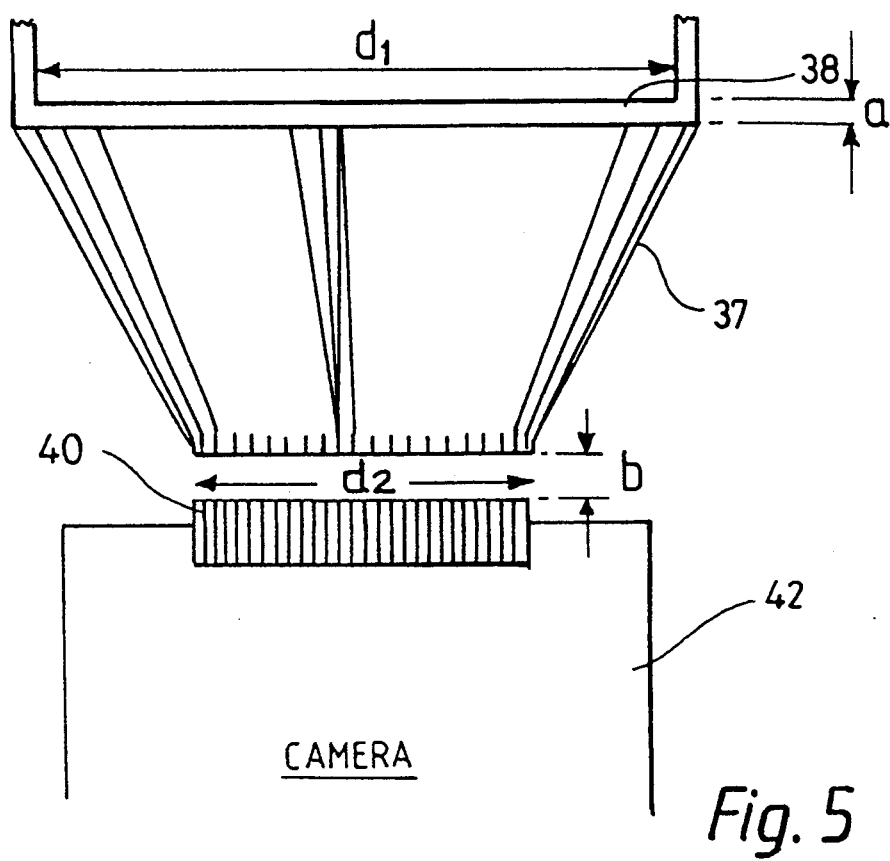
FIG. 5 illustrates a side view of an embodiment of the invention in which a large area petri dish can be viewed by a small area detector.
Figure 5A:
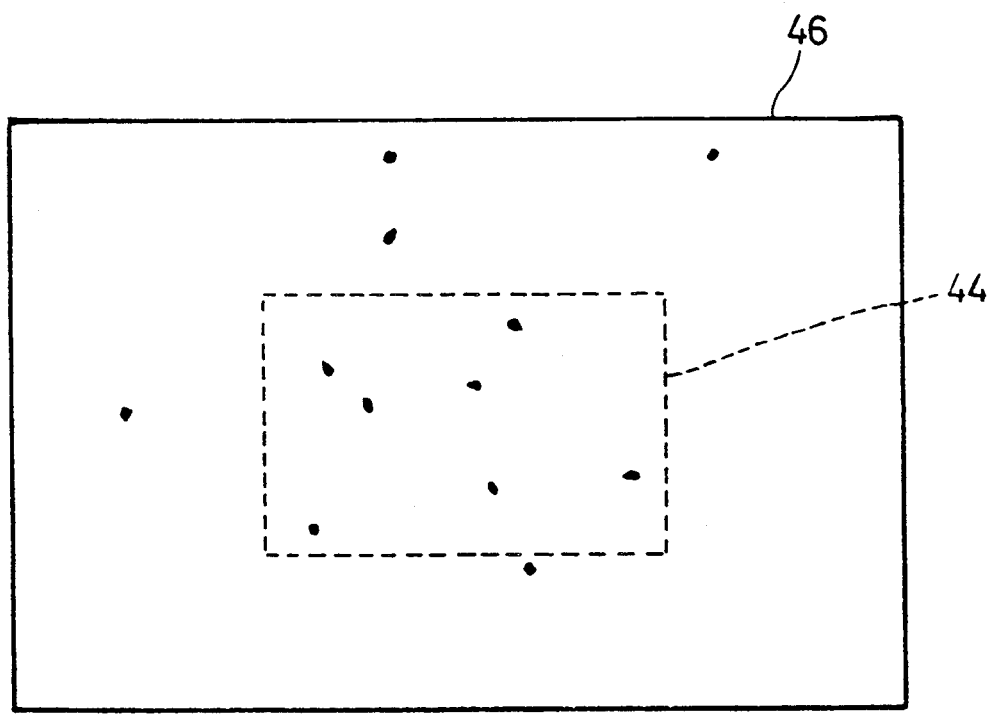
FIG. 5A is an example of an image as seen with the embodiment of FIG. 5.

If the petri dish base area is greater than that of the viewing window of the camera as shown in FIG. 5, then more of the dish area can be seen by the camera if a tapered fibre optic coupling plate 37 is provided between the dish and the camera. In FIG. 5 the diameter of the petri dish 38 is denoted by $d_1$ and that of the viewing window 40 (of the camera 46) is denoted by $d_2$. By selecting the taper so that the diameter of the smaller end of the tapered fibre optic coupling 37 is also $d_2$, it is found that all of the area of the petri dish 38 can now be viewed, albeit with greater demagnification. Whereas previously only the cells in the area 44 could be seen by the camera, now the cells from the whole area 46 can be viewed.

As a guide the two fields of view are shown in solid outline 11 and dotted outline 13 in FIG. 1.

Figure 6:
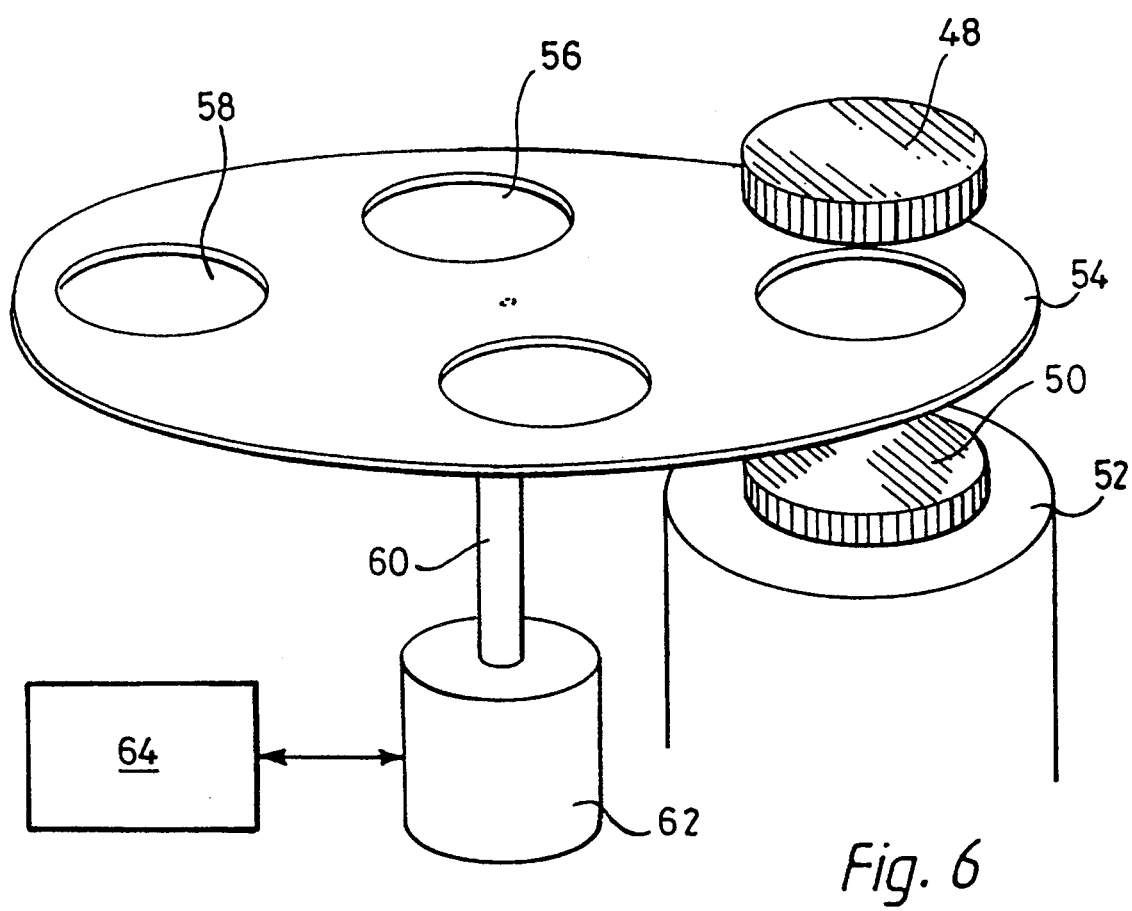
FIG. 6 is a perspective view showing how filters can be interposed between the dish and the faceplate of the invention.
Figure 7:
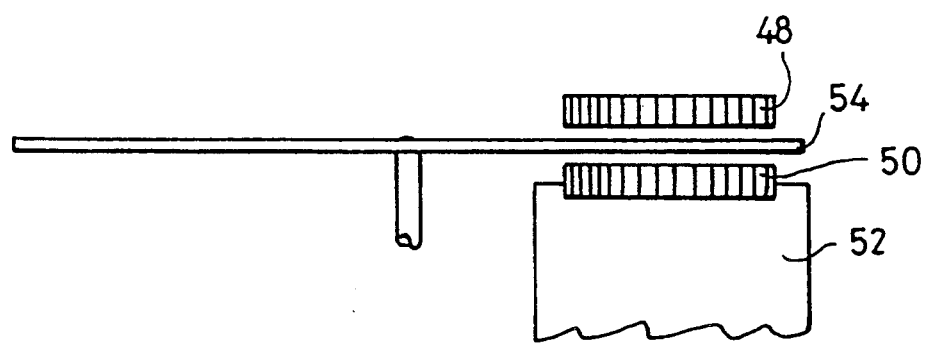
FIG. 7 is a side view which better shows the relative positions of the different elements in FIG. 6.

FIGS. 6 and 7 show how the invention allows filters to be interposed between the petri dish 48 and the viewing window 50 of a camera 52. To this end the air gap is utilised outlined and is partly occupied by a thin disc 54 containing apertures 56, 58 etc. thereon. One of these may simply comprise an opening, so that when it is aligned with the camera and dish, the set up is as described with reference to FIG. 3, and the other apertures contain filters. Alternatively all the apertures may include filters such as polarizing filters, wavelength selective filters and neutral density filters. By moving the disk 54 about a vertical axis 60 and providing a motor 62, so the disc can be rotated to bring appropriate apertures into alignment such as by control from a control unit 64 which may include a computer.

FIG. 7 shows the relative positions of the camera filter disc and dish.

We claim:

1. A light transmission system in which photon emission from material on a first surface is to be transferred to an optical detector, comprising a fibre optic face plate located between the first surface and the detector with a gap between the face plate and the detector, wherein the detector includes a fibre optic plate entry window which in combination with said fibre optic face plate forms a focused image of discrete photon emitting sites on the first surface of said detector.

2. A system as claimed in claim 1, wherein the detector is an image intensifier or an intensified CCD camera or a CCD detector or a cryogenically cooled CCD detector.

3. A system as claimed in claim 1, in which the first surface is a Petri dish or a microscope slide of plastics or glass.

4. A system as claimed in claim 1, in which there is one air gap between said first surface and the fibre optic face plate and another air gap between the face plate and said fibre optic plate entry window.

5. A system as claimed in claim 1, wherein a sample holder provides said first surface and the thickness $\underline{a}$ of the sample holder and the width $\underline{b}$ of the gap satisfy the relationship: $a/n_1 = b/n_2$
where $n_1$ and $n_2$ are the refractive indices of the two materials forming the sample holder and the gap respectively.

6. A system as claimed in claim 1, wherein a sample holder providing said first surface, the face plate and the detector are spaced and located so as to define at least one gap between the opposed faces of either the sample holder and the face plate or the latter and the detector, and an optical filter is removably located in the gap, the relative positions of the sample holder, face plate and detector being selected so that the optical path between the holder and the face plate is substantially the same as that between the face plate and the detector.

7. A system as claimed in claim 1, wherein a sample holder provides said first surface, and an optical filter is inserted between the sample holder and the detector.

8. A system as claimed in claim 1, further comprising a neutral density filter in the gap, whose attenuation is selected so as to control the quantity of light transmitted to the detector.

9. A system as claimed in claim 6, wherein the filter is a wavelength selective filter or a polarizing filter or a neutral density filter.

10. A system as claimed in claim 1, further comprising a rotatable or slidable carrier containing a plurality of different filters, the carrier being positioned between a sample holder which provides said first surface containing the photon emitting material and the face plate, or between the face plate and the plate entry window of the detector, to permit different filters to be inserted into the system.

11. A system as claimed in claim 1, wherein a shutter mechanism is positioned between a sample holder which provides said first surface and the face plate, or between the latter and the detector.

12. A system as claimed in claim 1, further comprising an LCD matrix positioned in the gap and electrically addressable to mask different areas of the sample holder.

13. A system as claimed in claim 1 wherein the material on said first surface includes lysing cells which emit photons when Adnosine TriPhosphate (ATP) is released therefrom.

14. A system as claimed in claim 1, wherein the material on said first surface includes cells together with luciferase and luciferin, and a lysing agent.

15. A system as claimed in claim 1 for investigating the infection of a monolayer of cells on a Petri dish, which comprises said first surface, with a genetically engineered virus which transmits lux and other genes into the genetic code of the cells.

16. A system as claimed in claim 11, wherein the shutter is combined with one or more filters.

17. A system as claimed in claim 1, wherein the detector comprises a CCD camera.

18. A system as claimed in claim 1, wherein the fibre optic face plate comprises a plate of glass formed from a uniform circular cross section bundle of optical fibres the cross section diameter of which is 50 mm and the length of the fibres making up the bundle is 3 mm and the two faces of the plate are parallel and are spaced apart by the length of the fibres and the fibres making up the plate are approximately 6 microns in diameter.

19. A method of detecting light emissions of a particular wavelength and/or polarisation from discrete regions on a support surface by means of a broad spectrum response detector coupled thereto by a face plate positioned between the support surface and the viewing window of a detector viewing window comprising a fibre optic face plate, comprising the steps of: inserting a neutral density filter during setting up so that light of all wavelengths and/or polarisations can pass from material on the support surface to the detector to allow setting up to occur, removing the neutral density filter, and replacing same with a wavelength selective and/or polarising filter and detecting whether any light of the selected wavelength and/or polarisation is being received by the detector, by inspecting the signal output of the detector.

* * * * *